(12) United States Patent
Rydberg et al.

(10) Patent No.: US 11,653,832 B2
(45) Date of Patent: May 23, 2023

(54) IMAGE ACQUISITION WITH REFLEX REDUCTION

(71) Applicant: Smart Eye AB, Gothenburg (SE)

(72) Inventors: Martin Rydberg, Gothenburg (SE); Per Sörner, Gothenburg (SE)

(73) Assignee: SMART EYE AB, Gothenburg (SE)

( * ) Notice: Subject to any disclaimer, the term of this patent is extended or adjusted under 35 U.S.C. 154(b) by 428 days.

(21) Appl. No.: 16/645,586

(22) PCT Filed: Sep. 19, 2018

(86) PCT No.: PCT/EP2018/075339
§ 371 (c)(1),
(2) Date: Mar. 9, 2020

(87) PCT Pub. No.: WO2019/057766
PCT Pub. Date: Mar. 28, 2019

(65) Prior Publication Data
US 2020/0281463 A1    Sep. 10, 2020

(30) Foreign Application Priority Data

Sep. 22, 2017    (EP) ..................................... 17192617

(51) Int. Cl.
| | | |
|---|---|---|
| *A61B 3/113* | (2006.01) | |
| *G06T 7/80* | (2017.01) | |
| *A61B 3/00* | (2006.01) | |
| *A61B 3/14* | (2006.01) | |
| *G06V 40/19* | (2022.01) | |

(52) U.S. Cl.
CPC ............ *A61B 3/113* (2013.01); *A61B 3/0008* (2013.01); *A61B 3/145* (2013.01); *G06T 7/80* (2017.01); *G06V 40/19* (2022.01)

(58) Field of Classification Search
None
See application file for complete search history.

(56) References Cited

U.S. PATENT DOCUMENTS

| | | | | |
|---|---|---|---|---|
| 6,088,612 | A * | 7/2000 | Blair .................... | A61B 1/0655 600/407 |
| 6,532,008 | B1 * | 3/2003 | Guralnick ............ | H04N 13/125 348/E13.058 |

(Continued)

FOREIGN PATENT DOCUMENTS

| | | |
|---|---|---|
| CN | 102984997 A | 3/2013 |
| CN | 104185858 A | 12/2014 |

(Continued)

OTHER PUBLICATIONS

Chinese Office Action for CN201880054627.1 that claims priority to the same parent application as the instant application; dated Dec. 14, 2021; 11 pages.

(Continued)

*Primary Examiner* — Kyle Zhai
(74) *Attorney, Agent, or Firm* — Harness, Dickey & Pierce, P.L.C.; Anthony G. Fussner (57) ABSTRACT

A method and system for acquiring images of a target area by acquiring (S1) a first image of the target area with a first image sensor; acquiring (S2) a second image of said target with a second image sensor; and preprocessing the first and second images by 1) performing a spatial 5 transform (S3) at least one of said first and second images in order to compensate for different image acquisition angles, and 2) at least partly removing (S4) undesired reflexes from the first and second images to form first and second reflex reduced images. With the present invention, it is still possible to eliminate or reduce 10 unwanted reflexes, even though the viewing angles of the two frames are different.

18 Claims, 7 Drawing Sheets

(56) References Cited

U.S. PATENT DOCUMENTS

| | | | |
|---|---|---|---|
| 9,866,820 B1 * | 1/2018 | Agrawal | H04N 13/239 |
| 2008/0084499 A1 * | 4/2008 | Kisacanin | A61B 5/18 |
| | | | 348/370 |
| 2012/0155726 A1 | 6/2012 | Li et al. | |
| 2013/0107214 A1 * | 5/2013 | Blixt | A61B 3/0008 |
| | | | 351/210 |
| 2014/0363064 A1 | 12/2014 | Lee et al. | |

FOREIGN PATENT DOCUMENTS

| | | |
|---|---|---|
| EP | 1349487 B1 | 9/2009 |
| EP | 2823751 A1 | 1/2015 |
| WO | WO-02/49506 A1 | 6/2002 |
| WO | WO-2015162605 A2 | 10/2015 |
| WO | WO-2016/027627 A1 | 2/2016 |

OTHER PUBLICATIONS

Seitz et al., A Comparison and Evaluation of Multi-View Stereo Reconstruction Algorithms; Dec. 31, 2006, 8 pages.
PCT International Search Report and Written Opinion for PCT/EP2018/075339 (published as WO2019/057766) that is the parent application to the instant application; dated Nov. 14, 2018, 14 pages.
European Search Report for European application No. 17192617.3 which is the parent application to the PCT application No. PCT/SE2018/075339, dated Mar. 23, 2018; 7 pages.

* cited by examiner

IMAGE ACQUISITION WITH REFLEX REDUCTION

This patent application is a U.S. national stage filing under 35 U.S.C. § 371 of PCT International Application No. PCT/EP2018/075339 filed Sep. 19, 2018 (published as WO2019/057766 on Mar. 28, 2019), which claims priority to and the benefit of European Application No. 17192617.3 filed Sep. 22, 2017. The entire contents of these applications are incorporated herein by reference.

FIELD OF THE INVENTION

The present invention relates to the field of head or eye detection, i.e. detecting and possibly tracking a target area of the head of a user, in particular the eyes, by means of image acquisition and processing. More specifically, the present invention relates to image acquisition in such systems.

BACKGROUND OF THE INVENTION

In some head/eye detection/tracking applications, multi-sensor imaging, i.e. imaging with at least two image sensors, is used on order to provide a more capable and reliable eye tracking. One specific advantage of multi-sensor imaging is that the distance to the target area can be determined. In multi-sensor imaging, images acquired simultaneously from two (or more) image sensors are combined to form one combined image frame, which is then used to establish the gaze (or point of regard) of the user.

However, it has been proposed in EP 2 823 751 to acquire images from two image sensors with a small separation in time. This approach allows use of different light sources (flash) for each image, providing advantages in the image processing, especially with respect to dark-pupil imaging which requires a certain minimum angular separation between sensor and light source. In EP 2 823 751, the two images are then treated as if they were acquired at the same time and combined in a conventional way to form one combined image frame.

Another potential problem with head/eye tracking is unwanted reflexes caused e.g. by glasses worn by the user. Unwanted reflexes may be caused by the illumination of the system, and may therefore have a relatively strong light intensity, and tend to disturb the head/eye tracking process. One approach to handle effects of unwanted reflexes in a single sensor system is presented in EP 1 349 487. According to this approach, alternating illumination is applied in consecutive image frames, and the consecutive image frames are then combined in a way that eliminates or reduces the unwanted reflexes. It would be desirable to reduce the effects of such reflexes also in multi-sensor eye tracking.

GENERAL DISCLOSURE OF THE INVENTION

It is a general object of the present invention to provide an improved or alternative multi-sensor head tracking method. Specific objects of the present invention include to reduce the effects of reflexes in multi-sensor head tracking.

According to a first aspect of the invention, there is provided a method for acquiring images of a target area of a head of a user, the method comprising the steps of providing a first image sensor and a second image sensor separated from each other by at least five centimeters, providing at least one light source arranged to illuminate the target area, acquiring a first image of the target area using the first image sensor and at least one of the at least one light source, and acquiring a second image of the target area using the second image sensor and at least one of the at least one light source. The method further comprises preprocessing the first and second images by performing a spatial transform at least one of the first and second images in order to compensate for different image acquisition angles, and at least partly removing undesired reflexes from the first and second images to form first and second reflex reduced images.

According to a second aspect of the invention, there is provided a system for acquiring images of a target area of a head of a user, comprising first and a second image sensor arranged at least five centimeters from each other and arranged to acquire images of the target area, at least one light source for illuminating the target area, an image acquisition controller configured to control the first image sensor to acquire a first image of the target area under illumination of at least one of the at least one light source, and control the second image sensor to acquire a second image of the target area under illumination of at least one of the at least one light source. The system further comprises processing circuitry configured to perform a spatial transform at least one of the first and second images in order to compensate for different image acquisition angles, and at least partly remove undesired reflexes from the first and second images to form first and second reflex reduced images.

The image reduced mages may be used to detect and/or track properties of the target area, e.g. properties of an eye, such as eye pose or direction of gaze.

It is noted that the "reflex reduced images" not necessarily are equivalent to the images acquired by the image sensors, but may be some other representation of these images.

In a single sensor system, as in EP 1 349 487, the two consecutive frames are acquired with the same sensor, ensuring that the viewing angle of the object is the same. However, a challenge with the method in EP 1 349 487 is that the frames will be separated in time (at least by the frame rate of the sensor) which introduces a potential movement of the object.

According to the present invention, these conditions are much reversed. By using two sensors, and as discussed in some detail in EP 2 823 751, the frames may be acquired with such a small time separation that any movement will be negligible and will not have to be taken into account for the purposes of eye tracking. In fact, in some implementations the images can be acquired at the same time instant. On the other hand, the sensors are separated in space, so that the viewing angle of the two frames used for forming a combined image will be different. The present invention is based on the surprising realization that, even though the viewing angles of the two frames are different, it is still possible to eliminate or reduce unwanted reflexes by using an appropriate spatial transform.

On a general level, the present invention relates to using information acquired from one image sensor to improve the quality of an image acquired by another image sensor. The inventors have realized the benefits of using this general principle for reducing reflexes in two different images acquired in a multi-sensor system. As the system inherently has more multiple sensors, the reflex reduction may be provided at essentially no added cost. The present invention thus enables improved tracking of a target area of an object even when the object is moving quickly and even when there are undesired reflexes, e.g. from eye glasses, present in the acquired frames.

It is here noted that "undesired" reflexes here relates to reflexes that do not contribute, and indeed interfere with, the detection of the target area. They should not be confused with intended reflexes in the target area, e.g. a glint reflection in the eye of a user, which are typically critical in order to provide satisfactory detection performance. The "undesired" reflexes may be caused by the illumination of the light source, but may also be caused by ambient lighting.

The separation between the sensors needs to be sufficient to allow identification and elimination of unwanted reflexes. Typically, this means an angular separation (i.e. angle formed between the two sensors and the target) of at least five degrees. In practical applications, where the distance between the sensors and the target is at least 0.5 meter, this means that the separation between the sensors should be at least five centimeters. In one specific example, the distance between sensors and target area is around 70 cm, and the separation between sensors is 8 cm, leading to an angular separation of $2 \times \tan^{-1}(4/70)=6.5$ degrees.

In one embodiment, one single light source is used during acquisition of both the first and the second images. This makes the system simple and cost efficient. If dark-pupil imaging is intended, the light source needs to be arranged off-axis, such that an angular separation between the single light source and each of said first and second image sensor is sufficient to provide a dark-pupil image. For a typical use case, that means at least five, or even at least eight, centimeters. In order to obtain a compact system enabling dark-pupil imaging with both sensors, it is advantageous to place the single light source equidistant from both sensors, so as to form a triangle.

In another embodiment, two different light sources are used during acquisition of the first and second images. In other words, the at least one light source includes a first light source and a second light source, and the first image is acquired using the first light source, and the second image is acquired using the second light source.

By using two light sources, a more compact system can be achieved. Also, it is possible to use different wavelengths for each sensor, thereby allowing for simultaneous imaging.

Preferably, the first image sensor and the second light source are located in a first location, and the second image sensor and the first light source are located in a second location. This ensures a very compact system, using the outer dimensions of the system for both separation of sensors and separation of light sources and sensors. With respect to placement of sensors and light sources, this system is similar to the system disclosed in EP 2 823 751.

By an image sensor and a light source being arranged in the same location is meant that they are arranged too close to each other to provide a satisfactory dark-pupil image. Conversely, by an image sensor and a light source being arranged in different locations is meant that they are arranged sufficiently far apart from each other to provide a satisfactory dark-pupil image.

The spatial transform can be based on intrinsic and extrinsic parameters of the image sensors, and may be performed iteratively by adjusting one or several unknown parameters, until a correlation measure between the two images is maximized.

In order to reduce the number of required iterations, the spatial transform can use an estimation of a distance between each image sensor and the target area as a starting approximation.

In one embodiment, the first image is spatially transformed and used to reduce reflexes in the second image, while the second image is spatially transformed and used to reduce reflexed in the first image.

In another embodiment, the first and second images are each transformed and compared with each other to provide a single reflex reduce image, and the single reflex reduced image is then reverse-transformed into the reflex reduced images.

It is noted that the present invention relates to all possible combinations of features recited in the claims.

BRIEF DESCRIPTION OF THE DRAWINGS

The present invention will be described in more detail with reference to the appended drawings, showing currently preferred embodiments of the invention.

FIG. 3b shows a front view of the image sensors and light source in FIG. 3a.

DETAILED DESCRIPTION OF PREFERRED EMBODIMENTS

In the following description, the target area of the head is an eye of the user, and the tracking system is an eye tracking system. However, the target area may equally well be any other area of the head.

Figure 1:
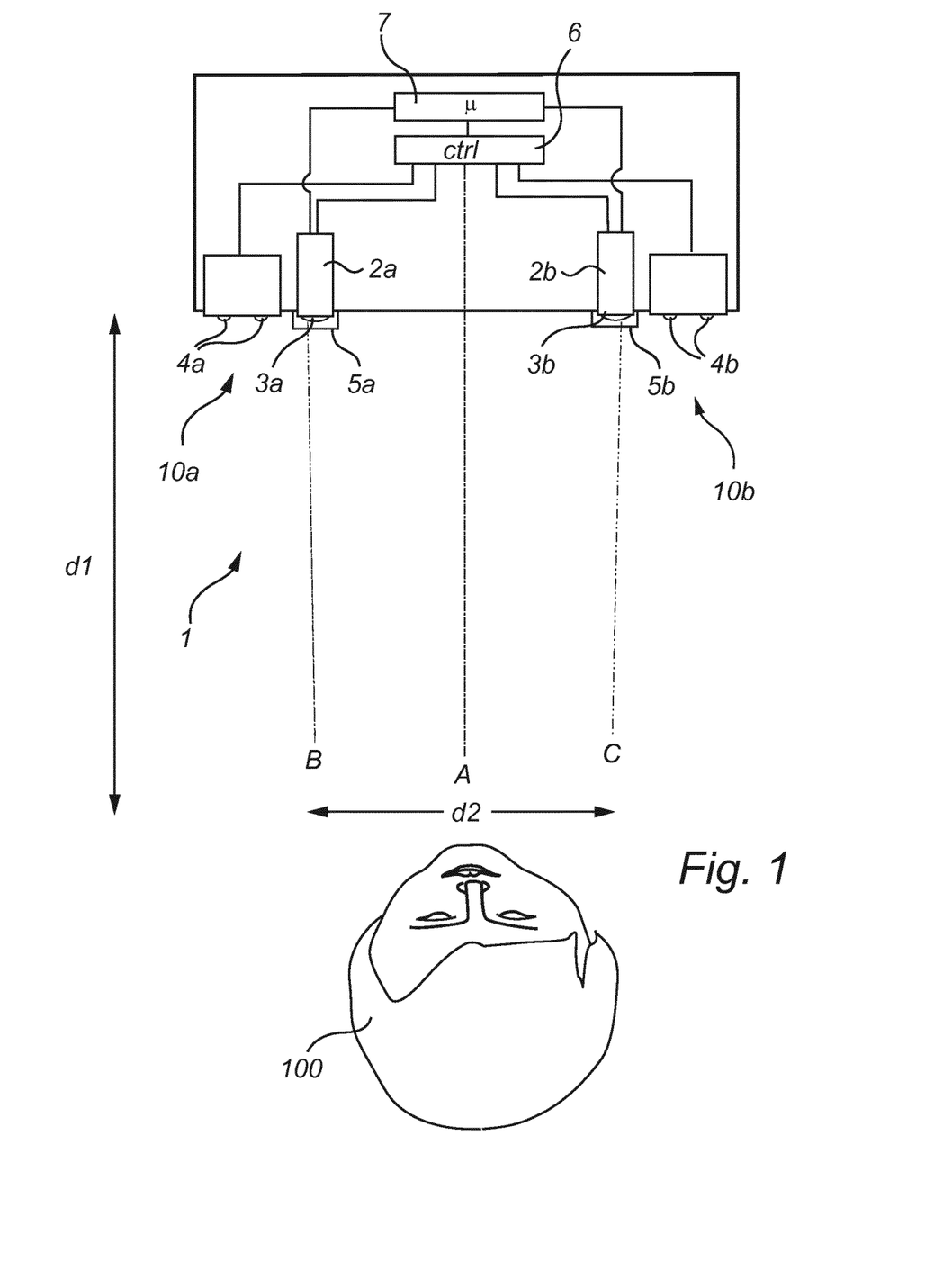
FIG. 1 shows a schematic top view of an eye tracking system according to a first embodiment of the invention.

FIG. 1 shows an eye tracking system 1 according to a first embodiment of the invention, arranged a distance $d_1$ from a user 100. The distance $d_1$ is normally in the range from 40 cm to 120 cm, and most typically "arm length", i.e. around 60-70 cm. The eye tracking device 1 includes two image sensors 2a, 2b, e.g. a CMOS image sensor, and suitable optics 3a, 3b.

The eye tracking device 1 has a central axis A, the first image sensor 2a has a first optical axis B, and the second image sensor 2b has a second optical axis C. In the illustrated example, the optical axes B, C are parallel with the central axis A, and are directed generally towards the user 100. In a different example, the optical axes B, C of the image sensors 2a, 2b may be arranged so as to converge slightly towards the central axis A. This may improve the image processing.

The distance $d_2$ between the first and second image sensors is selected sufficiently large for reflexes arising from illumination by the first and second light sources 4a, 4b to be distinguishable. The appropriate distance $d_2$ depends on the distance $d_1$, and under normal operating conditions the distance $d_2$ should be at least five cm. At the same time, it is normally desirable to avoid a too large separation, as it increases the dimensions of the system. So, a normal range of the distance $d_2$ is 5-12 cm, and as an example $d_2$ may be around 8 cm.

The system in FIG. 1 further includes two light sources 4a, 4b, typically configured to emit light outside the visible range such as infra-red (IR) or near infra-red (NIR). The light sources 4a, 4b may be solid state light sources, such as LEDs. In the illustrated example, the light sources 4a, 4b are LEDs configured to emit light with a light spectrum concentrated in a 50 nm band centered around 850 or 940 nm (NIR).

Each image sensor may further be provided with an optical band-pass filter 5a, 5b, e.g. an interference filter. The first and second filters 5a, 5b may be configured to have a pass-band substantially corresponding to the light emission spectrum of the light sources 4a, 4b. So, in the above mentioned example, the filters 5a, 5b should have a pass-band of around 825-875 nm, or 915-965 nm. The combination of narrow band light source and narrow pass-band filtering makes the image acquisition system less sensitive to surrounding light, e.g. sunlight.

In the illustrated example, the first image sensor 2a and the first light source 4a are arranged in a first location 10a, while the second image sensor 2b and the second light source 4b are arranged in a second location 10b. The first and second locations are located on opposite sides of the central optical axis A. The expression "same location" here indicates that the optical axis of the light source and the optical axis of the image sensor are too close to each other to provide a satisfactory dark-pupil image. Conversely, by an image sensor and a light source being arranged in different locations is meant that they are arranged sufficiently far apart from each other to provide a satisfactory dark-pupil image.

An image acquisition controller 6, henceforth referred to as the "controller" for brevity, is connected to the image sensors 2a, 2b and the light sources 4a, 4b, and is programmed to control the image sensors 2a, 2b to alternatingly acquire images under alternating illumination of the light sources 4a, 4b. More specifically, a light source 4a in one location 10a will be activated when an image is acquired by the image sensor 2b in the other location 10b. Similarly, the second light source 4b will be activated when an image is acquired by the first image sensor 2a.

One option is to have the light sources 4a, 4b constantly emitting light, and to arrange mechanical or optoelectrical shutters in front of the light sources 4a, 4b. The controller 6 can then activate a selected light source by opening the respective shutter.

Typically, however, in order to save energy and power consumption, the light sources are controlled to only emit light when the electronic shutter of the respective image sensor is open. As a practical example, the light sources 4a, 4b are triggered by pulses which have a duty cycle selected to provide sufficient illumination for acquiring one image frame. In other words, the pulse width corresponds to the time required for an image sensor to acquire one image.

Figure 2A:
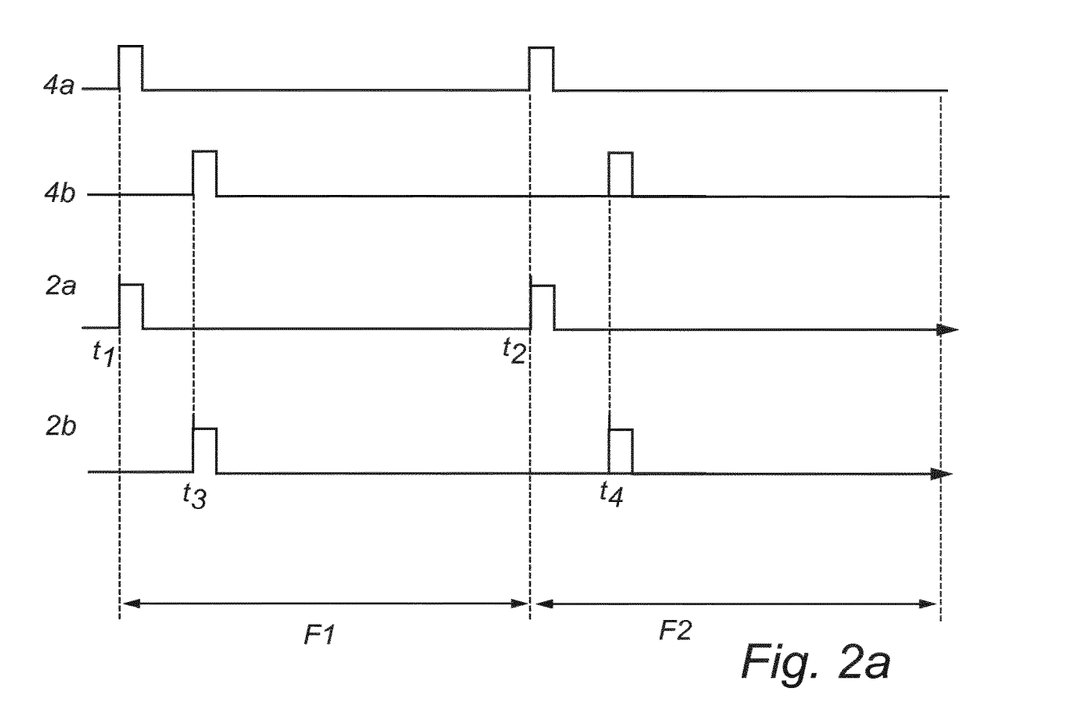
FIGS. 2a and 2b show two possible control schemes for the system in FIG. 1.

If identical light sources and filters 5a, 5b are used, the activation of the light sensors 2a, 2b will need to be separated by a small time distance, so that each image sensor only receives light form one light source. This time separation will typically be much smaller that the frame period, i.e. the time between consecutive frames F1, F2 in the tracking process. In practice, the separation is in the range 100 µs to 500 µs, while the frame period is in the order of ms, e.g. 20 ms for a 50 Hz frame rate. The pulse trains for each light source 4a, 4b will thus be slightly shifted in time with respect to each other, as illustrated in FIG. 2a. The controller 6 further controls the image sensors 2a, 2b to alternatingly acquire images in synchronization with the light pulses from the light sources 4a, 4b. In the example in FIG. 2a, the image sensor 2a will begin to acquire images at t1 and t2, while image sensor 2b will begin to acquire images in time instances t3 and t4. More details of this type of image acquisition process are disclosed in EP 2 823 751, herewith incorporated by reference.

Figure 2B:
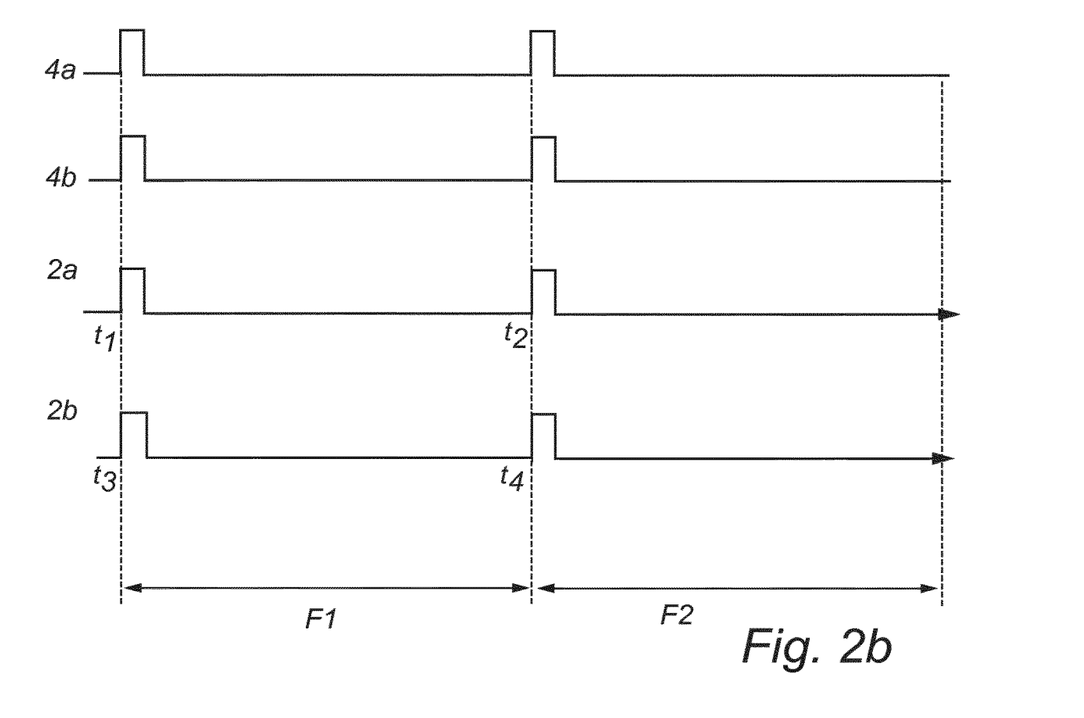

Alternatively, the light sources 4a and 4b have emission spectra in different wavelength areas, and the image sensors 2a, 2b are provided with corresponding filters 5a, 5b. In this case, there will be no "light leakage", and both light sources 4a, 4b may be activated at the same time, and images may be acquired by both image sensors 2a, 2b simultaneously in each frame F1, F2. In other words, t3=t1 and t4=t2. This control scheme is illustrated in FIG. 2b.

The eye tracking system 1 further comprises processing circuitry 7 connected to receive images 11a, 11b acquired by the image sensors 2a, 2b, and to process these images. The processing circuitry 7 may be integrated with the controller 6 or may be separate from the controller 6. In use, the eye tracking system 1 is arranged to acquire images of a target area of the eyes of the user 100. The processing circuitry 7 is configured to combine the images to form combined image frames, which are used to track movement in the eyes, in order to acquire various information. For example, the processing circuitry 7 may be programmed to obtain the direction of gaze of the user, or to detect drowsiness of the user.

Figure 3A:
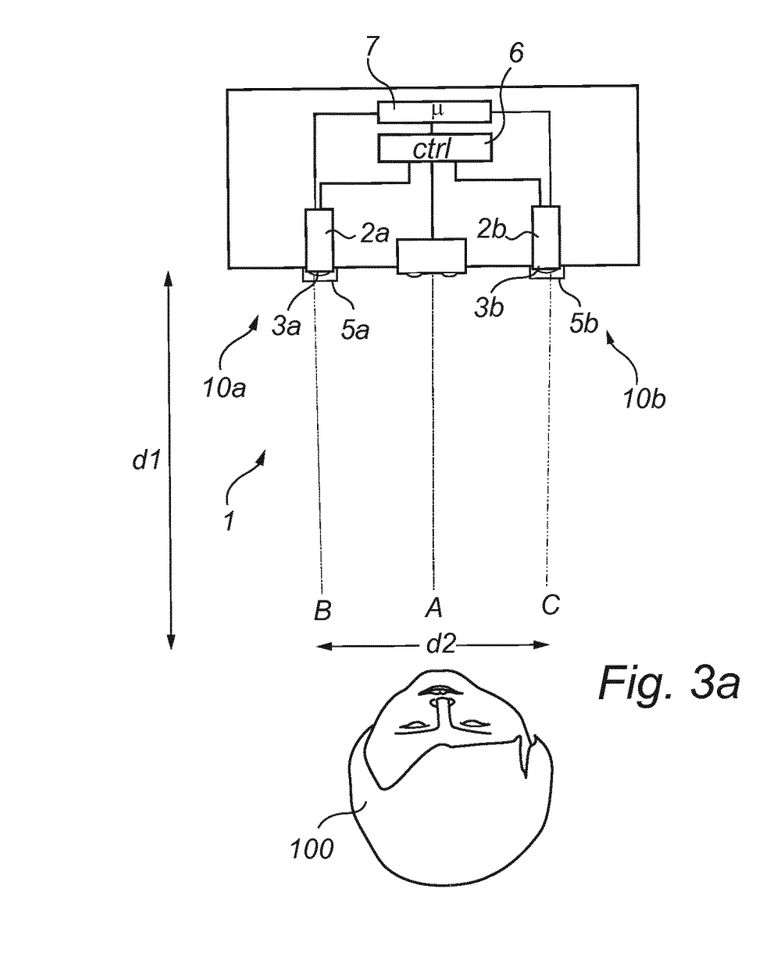
FIG. 3a shows a schematic top view of an eye tracking system according to a second embodiment of the invention.

FIG. 3a shows an eye tracking system 101 according to another embodiment of the present invention. Just as in FIG. 1, the system 101 comprises two image sensors 2a, 2b with optics 3a, 3b and optional filters 5a, 5b. The distances $d_1$ and $d_2$ are similar to those discussed above.

Figure 3B:
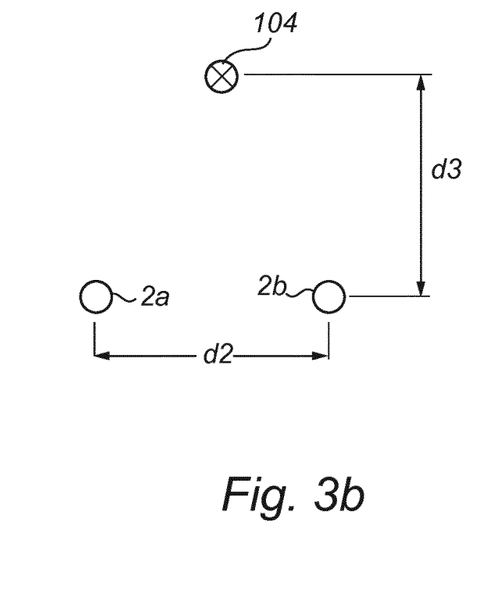

Contrary to system 1 in FIG. 1, the system 101 in FIG. 2 only has one light source 104, arranged in between the image sensors 2a, 2b. If it is desirable to increase the distance between each image sensor 2a, 2b and the light source 104, e.g. if dark-pupil processing is employed, it may be advantageous to separate the light source from the optical plane of the image sensors (i.e. the plane generated by the optical axis B and C) by a distance $d_3$, as illustrated in FIG. 3b.

Figure 4:
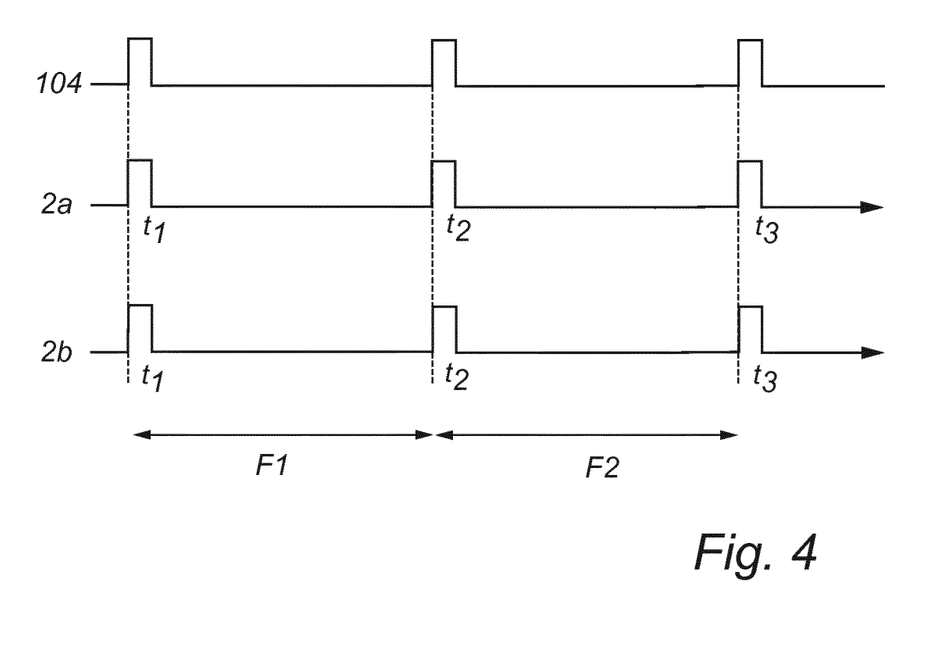
FIG. 4 shows a possible control scheme for the system in FIG. 3a-3b.

Similar to the controller 6 in FIG. 1, an image acquisition controller 106 is configured to control the image sensors 2a, 2b and light source 104 in the system 101. Here, however, as there is only one light source, both image sensors may be activated simultaneously. Also here, the light source 104 is preferably controlled by a pulsed signal with an appropriate duty cycle, and the image sensors are synchronized with the pulse signal. This is illustrated in FIG. 4, where the light sources 4a, 4b are both activated at instances t1 and t2 in frames F1 and F2, respectively.

The system 101 further has processing circuitry 7 similar to the processing circuitry in FIG. 1.

Figure 5:
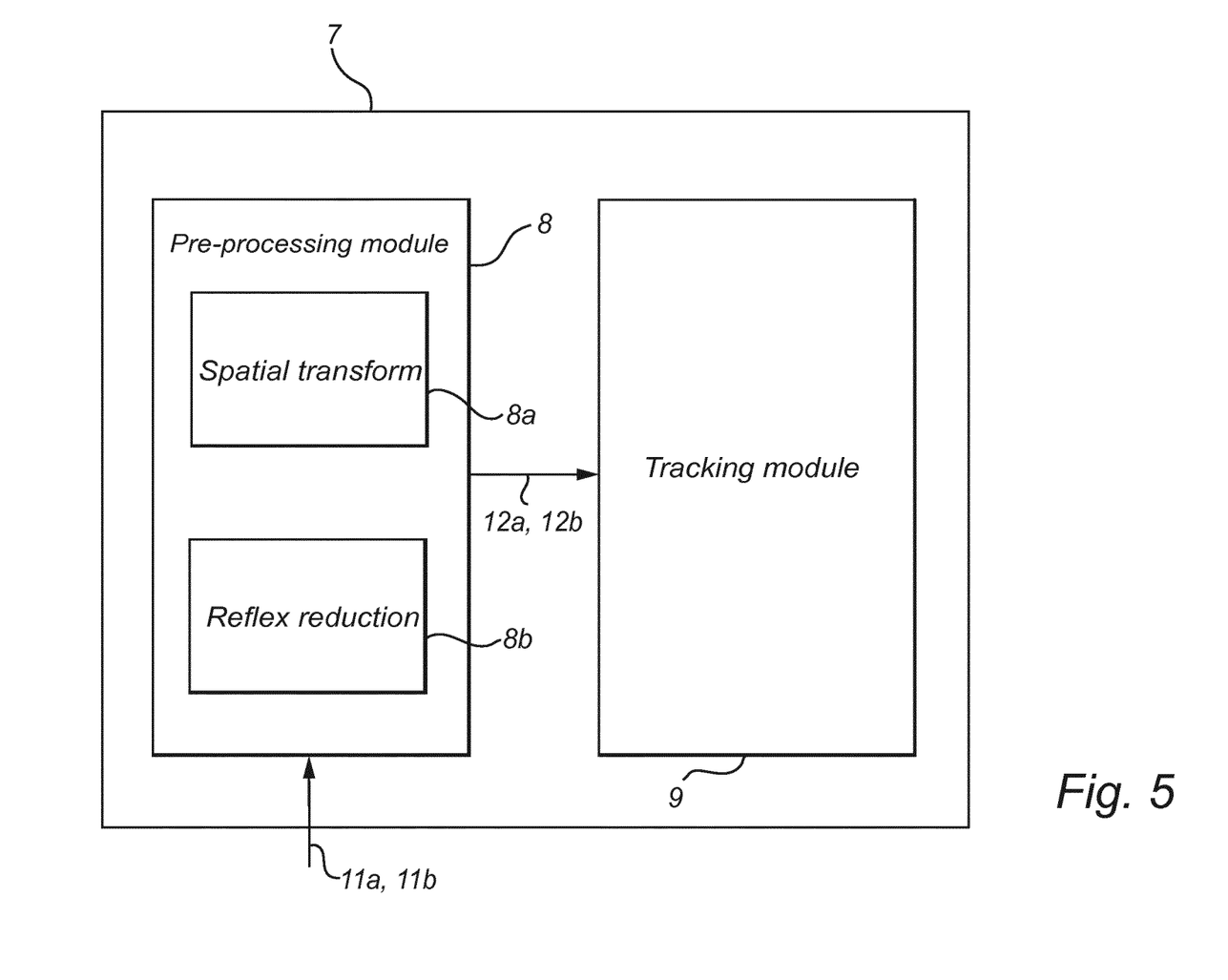
FIG. 5 is a functional block diagram of the processing circuitry in FIGS. 1 and 2a according to an embodiment of the invention.

FIG. 5 shows the processing circuitry 7 in more detail. The processing circuitry 7 includes a preprocessing module 8 and a tracking module 9. The preprocessing module 8 receives the acquired images 11a, 11b and includes an image transform function 8a for spatially transforming the images, and a reflex reduction/elimination function 8b to reduce or eliminate undesired reflexes from the images. The tracking module 9 uses the reflex eliminated images 12a, 12b to perform tracking of the target area (here eye or head tracking). The various parts of the processing circuitry 7 may be integrated into a single hardware or software unit, or as two or more separate hardware or software units. The processing performed by the various parts of the processing circuitry 7 will be discussed in more detail below.

Figure 6:
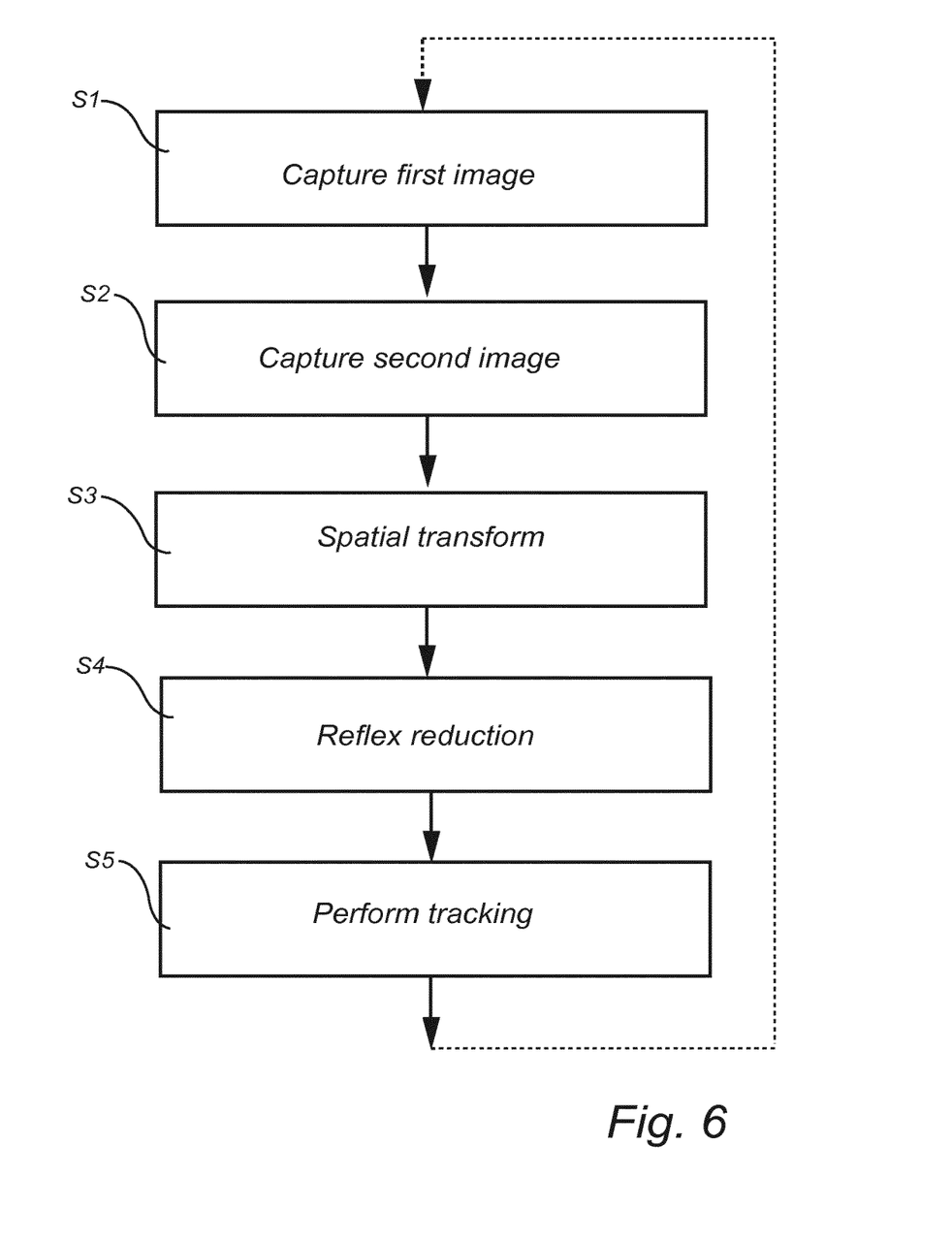
FIG. 6 is a flow chart of a method according to an embodiment of the invention.

With reference to FIG. 6, the operation of the eye tracking system 1, 101 will now be discussed. First, in step S1 a first image is captured using the first image sensor 2a, in synchronization with the second light source 4b (system 1) or the light source 104 (system 101). The user 100 is thus illuminated by the second light source 4b or light source 104, and light reflected from the target area is received by and stored in the first image sensor 2a (optionally after passing through the first filter 5a).

In step S2, a second image is captured using the second image sensor 2b, in synchronization with the first light source 4a (system 1) or the light source 104 (system 101). The second image is captured in a similar way to how the first image is captured. That is to say, the user 100 is illuminated by the first light source 4a or light source 104 and light reflected from the target area is received by and stored in the second image sensor 2a (optionally after passing through the first filter 5a).

As discussed above, depending on the design of the system, the two images may be acquired at the same time, or with a slight time separation, much smaller than the frame period.

In steps S3-S4, the preprocessing module 8 uses information from the stored first and second images in order to identify and remove (or at least reduce) undesired reflexes. Because of the spatial separation of the first and second image sensors 2a, 2b, the first and second images are acquired from different angles and possibly (in system 1) also with the target area being illuminated from different angles. Any undesired and potentially disturbing reflexes in the target area will therefore appear at slightly different places in the two images, and by using information from both images it is possible to identify the reflexes. The most problematic undesired reflexes are typically created by the illumination of the tracking system, but also ambient light may give rise to disturbing reflexes that may be reduced by the disclosed method.

First, in step S3, one or both of the images 11a, 11b are spatially transformed in order to compensate for the fact that the images have been acquired from different angles. Such a spatial transform of the images may be based on known information about extrinsic and intrinsic sensor parameters.

Here, the intrinsic parameters model the internal geometry and optical characteristics of the image sensor which determine how light is projected through the lens onto the image plane of the sensor, while the extrinsic parameters relate to the position and orientation of the sensors, e.g. the distance $d_2$ between sensors. The spatial transform may also be based on a model of the target area, e.g. of the eye of the user. The spatial transform can then be applied to one or both of the images and unknown parameters adjusted in an iterative process, until a correlation measure of the images is maximized.

The distance $d_1$ is one example of an unknown parameter. It is noted that the system will typically be able to provide an estimation of the distance d1 based on images from the two sensors 2a, 2b to be used as a starting approximation.

When the images have been spatially transformed, they can be treated as if they were acquired from the same position, and in step S4 they are compared pixel by pixel in order to remove undesired reflexes. Such a comparison may simple be a pixel-by-pixel selection of the lowest intensity from the two images. The result is a reflex reduced image, where bright areas occurring in only one image will have been removed. However, if one of the images is an untransformed (original) image, it may be advantageous to maintain as much as possible of this image. In that case, the comparison may be more complex, and e.g. include a threshold intensity difference in order to distinguish differences caused by an undesired reflex, and differences caused e.g. by shadows.

Note that the word "pixel" is here used as "picture element" not necessarily implying a digital image format. Both analog and digital signals may be used, and the comparison can be performed serially or in parallel, in hardware or in software.

Figure 7A:
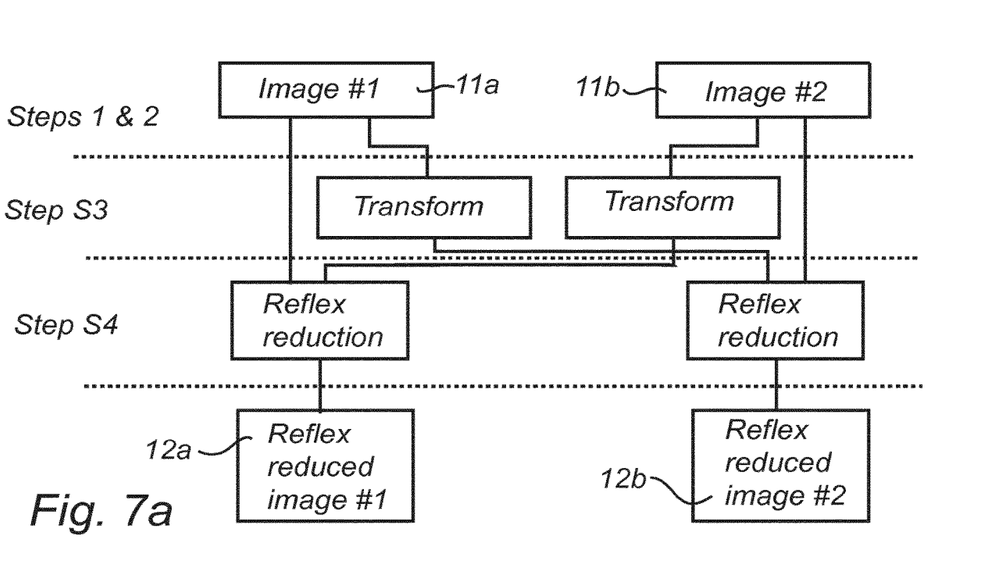
FIGS. 7a and 7b illustrate two examples of how steps S1-S4 in FIG. 6 may be performed.
Figure 7B:
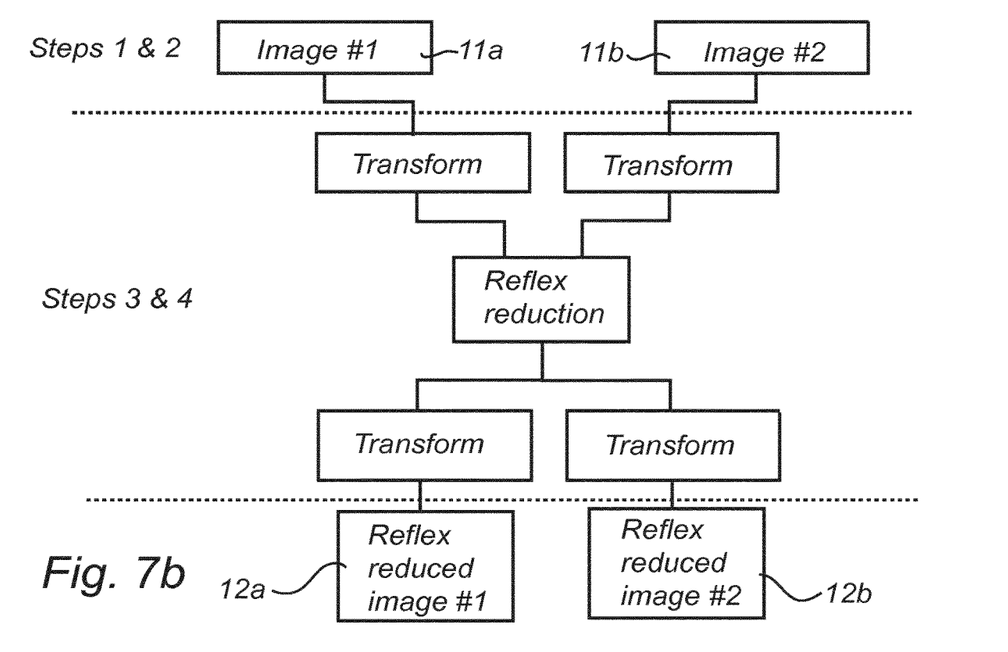

Several approaches are possible to use the above principles to obtain two reflex reduced images, and illustrated briefly in FIG. 7a-b.

In one approach (FIG. 7a), the first image 11a is spatially transformed and used to reduce reflexes in the second image 11b, while the second image 11b is spatially transformed and used to reduce reflexed in the first image 11b. With this approach, as much information as possible from the original image can be maintained in each reflex reduced image 12a, 12b.

In another approach (FIG. 7b) each image 11a, 11b is transformed (e.g. both images are transformed as if they had been acquired along the central axis A). The transformed images are compared to provide one reflex reduce image, which is then reverse-transformed into two reflex reduced images 12a, 12b.

In step S5, the tracking module 9 performs image processing using the reflex reduced images 12a, 12b to identify the target area in this particular frame. The tracking module 9 may for example analyze the images 12a, 12b and determine the location of the iris of the user or the direction of gaze by relating the location of the iris to the other points of the face. The processing may include a combination of the two images 12a, 12b to form a combined image frame, including information from both the first and the second image, but the processing may also treat the images individually.

By repeating the steps S1 through S5, the eye tracking system 1 is able to continuously track the target area, e.g. the direction of gaze.

The person skilled in the art realizes that the present invention by no means is limited to the preferred embodiments described above. On the contrary, many modifications and variations are possible within the scope of the appended claims. For example, it is clear that more than two image sensors may be used in some applications. If, for example, three image sensors are used, information from one sensor may be used to reduce or eliminate disturbing reflexes in images from the two other sensors. Or, an image from a first sensor may be used to reduce undesired reflexes in an image from a second sensor, the image from the second sensor may be used to reduce undesired reflexes in an image from a third sensor, and the image from the third sensor may be used to reduce undesired reflexes in the image from the first sensor.

The invention claimed is:

1. A method for acquiring images of a target area of a head of a user, said method comprising the steps of:
providing a first image sensor and a second image sensor separated from each other by at least five centimeters;
providing at least one light source arranged to illuminate the target area;
acquiring a first image of said target area using said first image sensor and at least one of said at least one light source;
acquiring a second image of said target area using said second image sensor and at least one of said at least one light source;
preprocessing the first and second images by:
performing a spatial transform of at least one of said first and second images in order to compensate for different image acquisition angles; and at least partly removing undesired reflexes from the first and second images to form first and second reflex reduced images;

wherein the method includes:
spatially transforming each said first and second images;
comparing picture elements of the spatially transformed first and second images; and
selecting the picture elements having the lowest intensity to thereby provide a single reflex reduced image in which any bright area(s) occurring in only one of said spatially transformed first and second images will have been removed.

2. The method according to claim 1, wherein said spatial transform is based on intrinsic and extrinsic parameters of the first and second image sensors.

3. The method according to claim 1, wherein said spatial transform is performed iteratively by adjusting one or several unknown parameters, until a correlation measure between the first and second images is maximized.

4. The method according to claim 3, wherein said spatial transform uses an estimation of a distance between each said first and second image sensor and the target area as a starting approximation.

5. The method according to claim 1, wherein the first image is spatially transformed and used to reduce reflexes in the second image, while the second image is spatially transformed and used to reduce reflexes in the first image.

6. The method according to claim 1, wherein the first and second images are each transformed and compared with each other to provide a single reflex reduce image, and then said single reflex reduced image is reverse-transformed into said first and second reflex reduced images.

7. The method according to claim 1, wherein said at least one light source is one single light source.

8. The method according to claim 1, wherein said at least one light source includes a first light source and a second light source, and wherein said first image is acquired using said first image sensor and said first light source, and said second image is acquired using said second image sensor and said second light source.

9. The method according to claim 8, wherein said first image sensor and said second light source are located in a first location, and said second image sensor and said first light source are located in a second location.

10. The method according to claim 1, wherein said first and second reflex reduced images are used to track properties of said target area.

11. A system for acquiring images of a target area of a head of a user, said system comprising:
a first and a second image sensor arranged at least five centimeters from each other and arranged to acquire images of the target area;
at least one light source for illuminating said target area;
an image acquisition controller configured to:
control the first image sensor to acquire a first image of said target area under illumination of at least one of said at least one light source, and
control the second image sensor to acquire a second image of said target area under illumination of at least one of said at least one light source;
processing circuitry configured to:
perform a spatial transform of at least one of said first and second images in order to compensate for different image acquisition angles, and
at least partly remove undesired reflexes from the first and second images to form first and second reflex reduced images;

wherein the processing circuitry is configured to:
spatially transform each said first and second images;
compare picture elements of the spatially transformed first and second images; and
select the compared picture elements having the lowest intensity to thereby provide a single reflex reduced image in which any bright area(s) occurring in only one of said spatially transformed first and second images will have been removed.

12. The system according to claim 11, wherein said at least one light source is one single light source.

13. The system according to claim 11, wherein said at least one light source includes a first light source and a second light source, and wherein said image acquisition controller is configured to acquire the first image using said first image sensor and said first light source, and acquire the second image using said second image sensor and said second light source.

14. The system according to claim 13, wherein said first image sensor and said second light source are located in a first location, and said second image sensor and said first light source are located in a second location.

15. The system according to claim 11, wherein said processing circuitry is further configured to track properties of said target area using said first and second reflex reduced images.

16. The system according to claim 11, wherein:
said at least one light source includes a first light source and a second light source;
said image acquisition controller is configured to acquire the first image using said first image sensor and said first light source, and acquire the second image using said second image sensor and said second light source;
said first image sensor and said second light source are located in a first location, and said second image sensor and said first light source are located in a second location; and
said first and second locations are on opposite sides of a central optical axis of the system.

17. A system for acquiring images of a target area of a head of a user, said system comprising:
a first and a second image sensor arranged at least five centimeters from each other and arranged to acquire images of the target area;
at least one light source for illuminating said target area;
an image acquisition controller configured to:
control the first image sensor to acquire a first image of said target area under illumination of at least one of said at least one light source, and
control the second image sensor to acquire a second image of said target area under illumination of at least one of said at least one light source;
processing circuitry configured to:
perform a spatial transform of at least one of said first and second images in order to compensate for different image acquisition angles, and
at least partly remove undesired reflexes from the first and second images to form first and second reflex reduced images;
wherein the processing circuitry is configured to:
spatially transform each said first and second images;
compare the spatially transformed first and second images pixel by pixel; and
select the compared pixels having the lowest intensity to thereby provide a single reflex reduced image in which any bright area(s) occurring in only one of said first and second images will have been removed.

18. A method for acquiring images of a target area of a head of a user, said method comprising the steps of:
provesproviding a first image sensor and a second image sensor separated from each other by at least five centimeters;
providing at least one light source arranged to illuminate the target area;
acquiring a first image of said target area using said first image sensor and at least one of said at least one light source;
acquiring a second image of said target area using said second image sensor and at least one of said at least one light source;
preprocessing the first and second images by:
performing a spatial transform of at least one of said first and second images in order to compensate for different image acquisition angles; and
at least partly removing undesired reflexes from the first and second images to form first and second reflex reduced images;
wherein the method includes:
spatially transforming each said first and second images;
comparing the spatially transformed first and second images pixel by pixel; and
selecting the pixels having the lowest intensity to thereby provide a single reflex reduced image in which any bright area(s) occurring in only one of said first and second images will have been removed.

* * * * *